United States Patent [19]

Brodner et al.

[11] Patent Number: 4,475,898

[45] Date of Patent: Oct. 9, 1984

[54] FETAL VENTRICULO-AMNIOTIC SHUNT

[75] Inventors: Robert A. Brodner, Paoli, Pa.; Robert S. Bley, Santa Barbara; Ray H. Dormandy, Jr., Goleta, both of Calif.

[73] Assignee: American Hospital Supply Corporation, Evanston, Ill. ; a part interest

[21] Appl. No.: 371,756

[22] Filed: Apr. 26, 1982

[51] Int. Cl.³ .............................................. A61M 25/00
[52] U.S. Cl. ........................................ 604/9; 604/247
[58] Field of Search ....................................... 604/8–10, 604/247, 256

[56] References Cited

U.S. PATENT DOCUMENTS 3,020,913  2/1962  Heyer .......................................... 604/9
3,313,299  4/1967  Spademan ................................. 604/167
3,894,541  7/1975  El-Shafei .................................. 604/10
4,230,119  10/1980 Blum ...................................... 604/8 X
4,375,816  3/1983  Labianca .................................. 604/8

4,413,985 11/1983 Wellner et al. .......................... 604/9

Primary Examiner—Dalton L. Truluck
Attorney, Agent, or Firm—Roger A. Williams

[57] ABSTRACT

A fetal shunt is disclosed which comprises a tubular body having a proximal end and a distal end. The proximal end is provided with openings which extend into a lumen which forms a fluid-flow passageway extending between the proximal and distal ends. Either flanges or inflatable cuffs, which can be inflated to form a balloon extending around the tubular body, are provided intermediate the length of the tubular body. The outwardly projecting flanges or the inflated cuff portions form projections which maintain the position of the fetal shunt after it is implanted. The distal end of the tubular body of the shunt is provided with a valve for permitting fluid flow outwardly of the tubular body. The shunt provides a method for transferring cerebral spinal fluid from the fetal cranium to the amniotic fluid surrounding the fetus.

12 Claims, 5 Drawing Figures

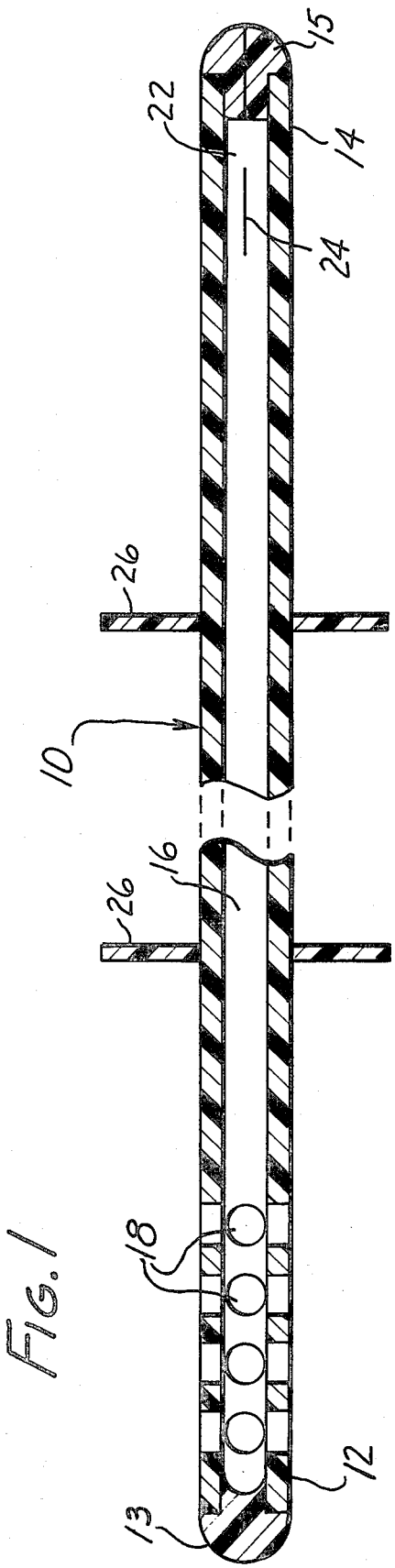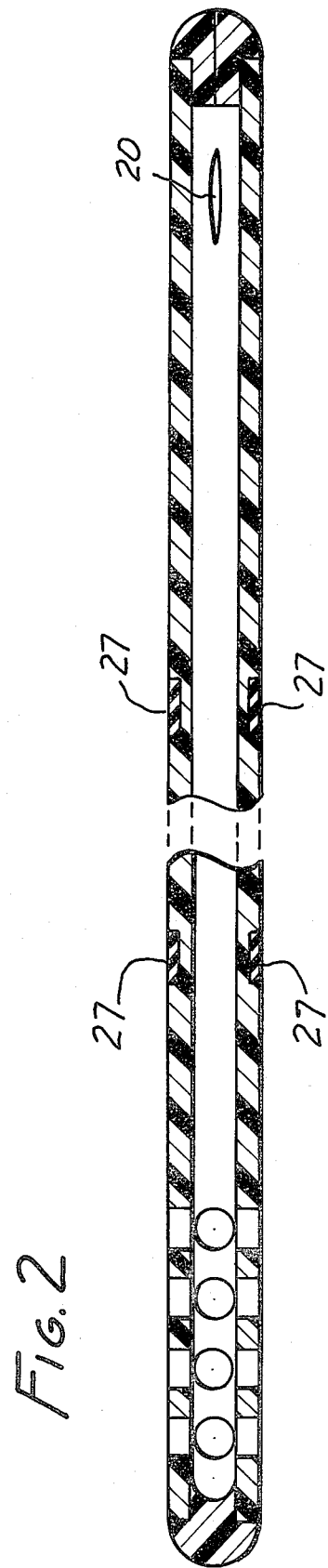

FETAL VENTRICULO-AMNIOTIC SHUNT

BACKGROUND OF THE INVENTION

The invention herein relates to a medical shunting device for transferring cerebral spinal fluid (CSF) from the ventricles of the brain to a remote location. In particular, the invention herein relates to a fetal ventriculo-amniotic shunt for transporting CSF from the ventricles of the fetus to the amniotic fluid within the womb of the fetus's mother.

With the increasing development of knowledge in the medical and health care field, attention has been recently directed to the study of fetal development. It is accepted that an important determinant in an individual's health is the development of the fetus during pregnancy. That is, when there is a normal fetal development, there is a strong likelihood of good health in the baby when born.

The fetus has been considered inviolable and medically isolated in the protectorate of the material womb for many years. However, as medical knowledge has increased, prenatal diagnostic techniques have evolved to such sophistication that most fetal diseases can be accurately defined and diagnosed. Following the definition and diagnosis of fetal diseases, various methods of treatment of such diseases has also been developing. Such treatments include the development of innovative surgical techniques and medical devices for direct corrective therapy of defective fetuses.

Congenital hydrocephalus is a common defect among children with an incidence of about 1.5 per one thousand live births. As pregnancies at an older maternal age are increasing, the incidence of central nervous system malformations of all types has also been found to be increasing. Congenital hydrocephalus is developed in utero and causes progressive attenuation of the fetal brain resulting in the birth of a severely handicapped individual.

In many instances of congenital hydrocephalus, the treatment consists of shunting the extra and unnecessary CSF from the ventricles of the brain to either the heart or peritoneal cavity. However, such treatment is practiced on the individuals following birth.

Prenatal shunting represents a preventative treatment which can protect the developing brain and allow the birth of a more healthy newborn infant. Prenatal shunting of a hydrocephalic fetus can protect the developing brain from the damaging effects of elevated intraventricular pressure during gestation. This treatment can be entirely preventative as it can preserve the fetal cortical mantle and lead to the birth of a more functional and healthy individual. In utero shunting represents a new therapeutic option to abortion or inaction once fetal hydrocephalus is diagnosed.

SUMMARY OF THE INVENTION

The invention herein relates to a fetal ventriculo-amniotic shunt. The shunt herein is a tubular conduit made of silicone with an inner lumen for conveying the cerebro spinal fluid (CSF) from the venticles of the fetus to the amniotic fluid within the uterus of the fetus's mother. The shunt has a proximal end with openings provided thereon which extend into the lumen. The proximal end of the shunt is placed within the ventricles of the brain of the fetus. The shunt extends through the developing skull of the fetus and terminates at a distal end within the amniotic fluid sac of the uterus. The distal end of the shunt can be provided with a opening for permitting the flow of the CSF through the lumen and shunt and into the amniotic fluid. The distal end can also be provided with a valve which permits the flow of CSF outwardly of the shunt while inhibiting the flow of amniotic fluid inwardly and into the shunt's lumen.

Positioned along the shunt are two flanges for maintaining the shunt in position in the fetus. The flanges can be permanent flanges extending outwardly of the shunt or can be inflatable flanges or balloons which are inflated after the shunt is implanted within the fetus. The flanges are positioned along the length of the shunt such that one flange will be within the fetus and one flange will remain outside the fetus. The two flanges thereby cooperate to reduce movement of the shunt and thereby tend to maintain the shunt in position once it is implanted.

BRIEF DESCRIPTION OF THE DRAWINGS

FIG. 1 is a cross-sectional view of an embodiment of a fetal ventriculo-amniotic shunt;

FIG. 2 is a cross-sectional view of a second embodiment of a fetal ventriculo-amniotic shunt herein;

DETAILED DESCRIPTION

Figure 3:
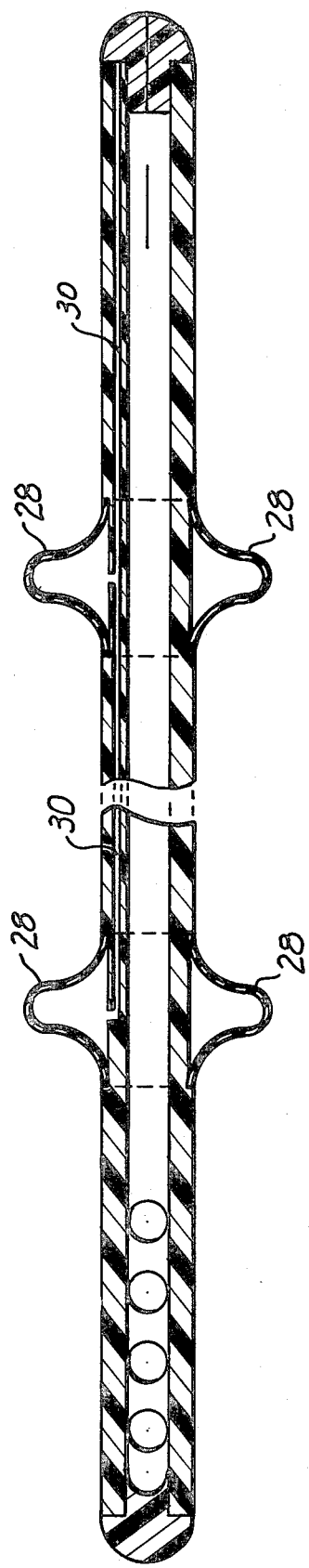
FIG. 3 is a cross-sectional view of a third embodiment of a fetal ventriculo-amniotic shunt.

The fetal ventriculo-amniotic shunt will be described with regard to the accompanying drawings. With regard to FIG. 1, an embodiment of a fetal ventriculo-amniotic shunt is shown. The fetal ventriculo-amniotic shunt 10 is shown in cross section. The shunt is tubular and has a proximal end 12 and a distal end 14. A lumen 16 extends the length of the shunt. End plugs 13 and 15 block the lumen at the proximal and distal ends respectively.

The fetal ventriculo-amniotic shunt can be constructed of any suitable biocompatible material. In a working embodiment of the shunt, the shunt was constructed of silicone.

The proximal end of the shunt is inserted into the fetal cranium. The proximal end is provided with at least one opening 18 for receiving the CSF present within the ventricle of the fetus. Preferably, a plurality of openings 18 are provided on the proximal end to allow for the CSF to enter the lumen of the shunt. The openings 18 extend through the wall of the shunt into the lumen. In a working embodiment, eight openings were provided on the proximal end having a diameter of 0.027 inches each.

The distal end 14 of the shunt is provided with a distal end plug 15. The distal end plug can be perforable or provided with a slit opening or needle track to receive a stylet. When a stylet is inserted through such a distal plug, then withdrawn, the distal end plug closes, forming a barrier to fluid flow.

The distal end is provided with an opening, as shown in the embodiment of FIG. 2, or as shown in the embodiment of FIG. 1, a valve 22. Still referring to FIG. 1, the valve shown therein can be a slit valve 24 extending laterally along the distal end. The slit valve can have one or more laterally extending slits along the distal end. Both the opening 20 or valve 22 function to permit the flow of CSF outwardly of the shunt. The valve 22 can be a unidirectional valve permitting the CSF to flow only outwardly of the shunt. The embodiment shown in FIG. 2 can permit fluid flow either inwardly or outwardly of the shunt body.

In shunts wherein a valve 22 is provided on the distal end, the valve can be formed such that it will open to fluid flow when a fluid pressure is formed within the lumen of the shunt. For example, shunts can be made having valves that open at 40 to 60 millimeters of water or 60 to 80 millimeters of water. The ability to make shunts which open at varying pressures provides a versatility to the shunts so that the shunts can be tailored to particular needs of a particular fetus.

Intermediate the length of the shunt and attached thereto is at least one, and preferably two, flanges 26. In the embodiment shown in FIG. 1, the flanges extend around the body of the shunt. The flanges can be stiff or flexible, but preferably are flexible to facilitate insertion of the shunt into the fetus. The flanges serve to position the shunt within the fetus.

The flange near the proximal end is inserted into the fetal cranium and helps in maintaining the proximal end of the shunt within the ventricle. The flange near the distal end remains outside the fetus and also aids in maintaining the position of the shunt once it is implanted.

The primary purpose of the flanges is for anchoring the shunt in position within the fetal cranium. The proximal flange serves to keep the shunt within the ventricle and counteracts the intraventricle pressure in the hydrocephalic fetus. In many instances, such pressure is in the range of 55 to 100 millimeters of water. The distal flange prevents the shunt from being pushed into the ventricle by pressure within the amniotic cavity. Generally, the amniotic cavity pressure is about 0 to 1 centimeter of water. These pressures can vary markedly during uterine contractions.

A working embodiment of the shunt shown in FIG. 1 has been constructed having a length of 2.80 inches. The shunt had an outside diameter of 0.052 inches and the lumen had an inner diameter of 0.027 inches. The distance from the proximal end of the shunt to the flange nearest the proximal end was 0.40 inches. The distance from the distal end to the flange nearest the distal end was 0.40 inches. The proximal end was provided with eight holes each having a diameter of 0.027 inches. The outwardly extending flanges were circular in shape having a diameter of 0.172 inches. The flanges were 0.005 inches in thickness.

The shunt is implanted through an incision in the abdominal wall and uterine myometrium which exposes the fetal cranium. A trocar can be used to provide a passageway into the fetal cranium. A cannula can be introduced through the passageway into the fetal cranium after the trocar has been removed. A stylet can be inserted into the distal plug 15 of the shunt and used to move the shunt through the cannula and into the fetal ventricular system. When the proximal end of the shunt is properly positioned within the ventricle, the stylet can be withdrawn and the shunt's proximal flange can serve to anchor the shunt within the ventricle. The cannula can then be removed and the skin incision closed.

With reference to FIG. 2, another embodiment of a fetal ventriculo-amniotic shunt is shown. The shunt shown in FIG. 2 is similar in all characteristics to the embodiment shown in FIG. 1 with the exception that the embodiment of FIG. 2 has an opening 20 at the distal end as opposed to a valve.

The embodiment shown in FIG. 2 also differs from the embodiment shown in FIG. 1 in that there are no permanent outwardly extending flanges in the embodiment of FIG. 2. Positioned along the body of the shunt in FIG. 2 are two inflatable cuff portions 27. The inflatable cuff portions can be suitably inflated by introducing a fluid into the cuff portions to form outwardly projecting balloons or inflated cuffs which serve the same purpose as the flanges in the embodiment shown in FIG. 1. The embodiments shown in FIGS. 3 and 4 illustrate shunts having such an inflatable cuff structure.

With reference to FIG. 3, one embodiment of an inflatable cuff fetal ventriculo-amniotic shunt is illustrated. The embodiment shown in FIG. 3 has outwardly extending and inflated balloons 28 which extend around the shunt's body. The inflated balloons 28 function to maintain the shunt in place as was discussed above with regard to the outwardly extending flanges 26.

The balloons 28 can be inflated through a second lumen 30 extending through and along the side wall of the shunt body. The second lumen can be accessed with a syringe or other instrument at the distal end of the shunt. For example, a syringe can be inserted into the second lumen 30 at the distal end and an inflationary fluid introduced through the second lumen to the two cuff portions to inflate them and form the two balloons 28.

Figure 4:
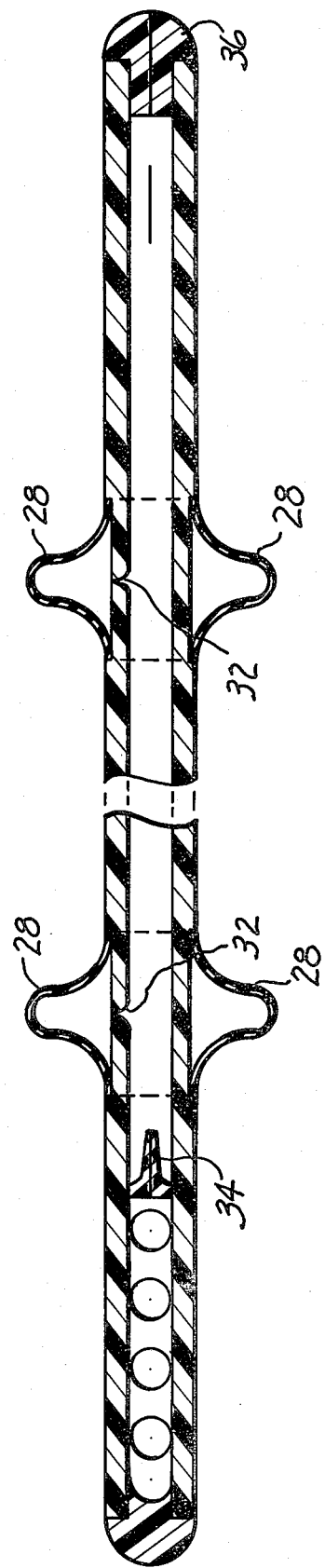
FIG. 4 is a cross-sectional view of a fourth embodiment of a fetal ventriculo-amniotic shunt.

FIG. 4 shows another embodiment of the fetal ventriculo-amniotic shunt with inflationary balloons 28. The system for inflating the balloons 28 differs from that of the embodiment shown in FIG. 3.

The embodiment illustrated in FIG. 4 is provided with a one-way valve, such as a miter valve 34, near the proximal end. The body of the shunt is provided with one-way valves 32 positioned therealong at the locations of the inflatable cuff portions of the shunt. The valves 32 provide fluid flow from the lumen into the inflatable cuff portions. A cannula of a syringe or an inflationary stylet can be introduced through the distal plug 36. An inflationary fluid can be introduced to the lumen of the shunt through such a stylet. As the fluid flows along the lumen, it encounters the valve 34. The inflationary fluid cannot flow through the valve as the fluid flow through the valve 34 is in the opposite direction; i.e., from proximal to distal. The fluid then flows through the valves 32 into the inflationary cuff portions, thereby inflating the cuff portions, forming the encircling balloons 28. Once the balloons are inflated, the syringe or stylet can be withdrawn through the distal plug 36 which seals upon itself. Pressure within the fetal cranium due to CSF can be released as the CSF can flow through the provided openings at the proximal end through the valve 34, through the lumen and outwardly of the slit valve at the distal end.

Figure 5:
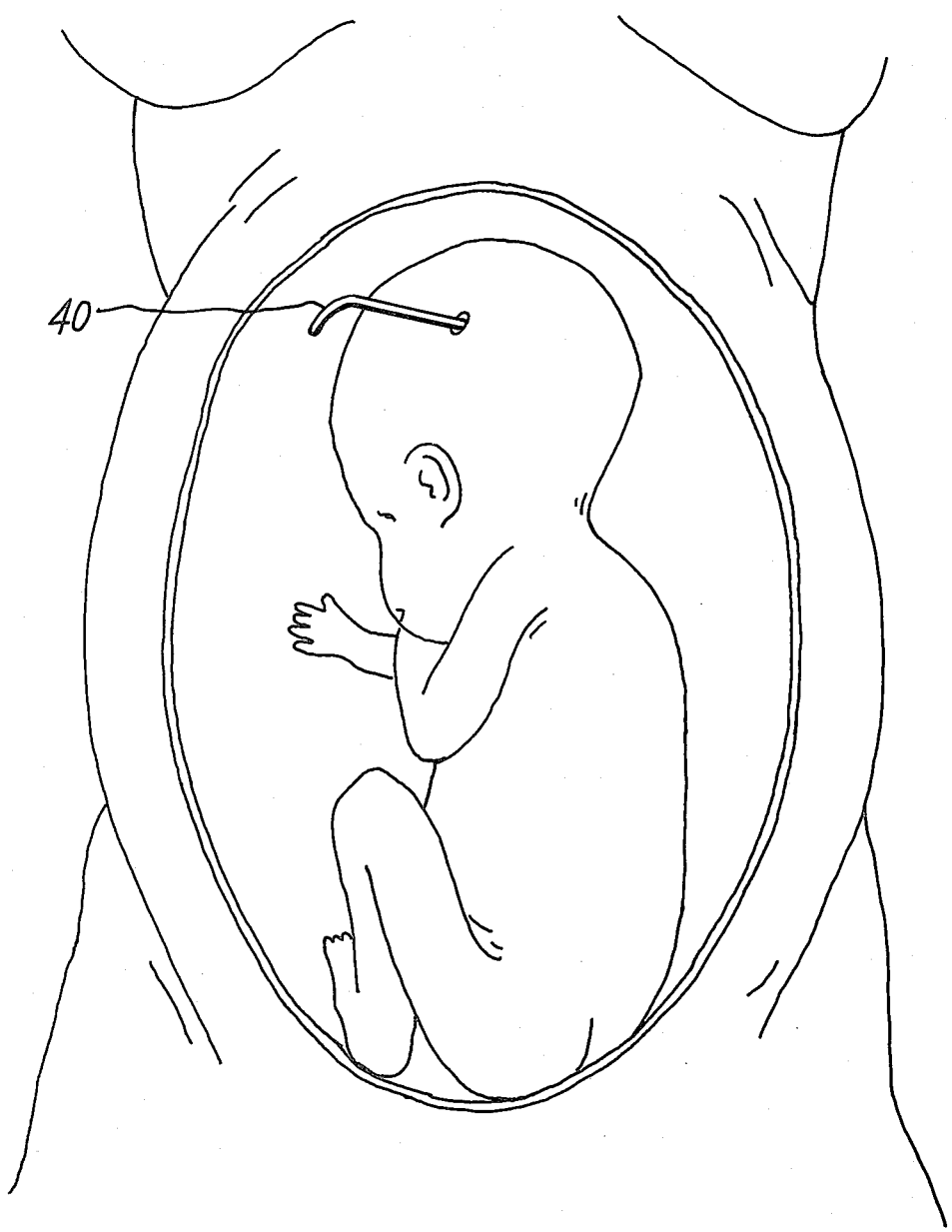
FIG. 5 is a schematic illustration showing the positioning of a fetal ventriculo-amniotic shunt in the fetus within the maternal womb.

A schematic representation of an implanted fetal ventriculo-amniotic shunt is illustrated in FIG. 5. The fetal ventriculo-amniotic shunt 40 is shown implanted within the fetal cranium. The distal end of the shunts herein described can be angled as is shown in FIG. 5. Such an angulation to the distal end may avoid some complications due to fetal movement.

We claim:

1. A fetal ventriculo-amniotic shunt comprising:

a flexible tubular integral body having a lumen forming a fluid-flow passageway extending through the tubular body;

the tubular body having a proximal end with provided openings extending into the lumen and having a distal end;

plug means on the distal end for providing a perforable and self-sealing barrier to fluid flow;

fluid-flow means positioned on the distal end for permitting fluid flow from the lumen; and positioning means on the tubular body which extends outwardly of the tubular body for providing placement fixation when the shunt is introduced into a fetus.

2. A fetal ventriculo-amniotic shunt as recited in claim 1 wherein the fluid-flow means comprises openings provided on the distal end.

3. A fetal ventriculo-amniotic shunt as recited in claim 1 wherein the fluid-flow means comprises a valve on the distal end.

4. A fetal ventriculo-amniotic shunt as recited in claim 3 wherein the valve comprises a one-way valve permitting fluid flow outward of the shunt.

5. A fetal ventriculo-amniotic shunt as recited in claim 1 wherein the positioning means comprises at least one outwardly projecting flange attached to and extending around the tubular body of the shunt.

6. A fetal ventriculo-amniotic shunt as recited in claim 1 wherein the positioning means comprises at least one inflatable cuff portion on the tubular body, which cuff portion can be inflated by introducing an inflationary fluid to expand the cuff portion, forming an outwardly extending balloon around the tubular body.

7. A fetal ventriculo-amniotic shunt as recited in claim 6 wherein two inflatable cuff portions are provided on the tubular body of the shunt.

8. A fetal ventriculo-amniotic shunt as recited in claim 6 wherein a second lumen extends through the tubular body from the distal end to such inflatable cuff portion.

9. A fetal ventriculo-amniotic shunt as recited in claim 6 further comprising a one-way valve positioned within the lumen proximal to the inflatable cuff portion and which permits fluid flow distally therethrough and valve means adjoining the lumen and such inflatable cuff portion for permitting fluid flow from the lumen into such inflatable cuff portion.

10. A fetal ventriculo-amniotic shunt comprising:
a flexible tubular integral body having a proximal end and a distal end with a lumen extending between the distal and proximal ends;

the proximal end provided with openings extending into the lumen;

a one-way valve provided on the distal end for permitting fluid flow outwardly of the tubular body;

a perforable and self-sealing distal plug on the distal end;

a distal flange projecting outwardly of the tubular body; and a proximal flange projecting outwardly of the tubular body.

11. A fetal ventriculo-amniotic shunt comprising:
a flexible tubular integral body having a proximal end and a distal end;

the proximal end having provided openings extending into a lumen which forms a fluid-flow passageway extending between the proximal and distal ends;

a perforable and self-sealing distal plug within the lumen at the distal end of the tubular body;

two inflatable cuff portions extending around the tubular body;

a second lumen in the tubular body extending from the distal end to the inflatable cuff portions and in fluid flow communication with such cuff portions; and a valve on the distal end for permitting fluid flow outwardly of the tubular body.

12. A fetal ventriculo-amniotic shunt comprising:
a flexible tubular integral body having a proximal end and a distal end;

the proximal end having provided openings extending into a lumen which forms a fluid-flow passageway between the proximal and distal ends;

a perforable and self-sealing distal plug within the lumen at the distal end;

two inflatable cuff portions extending around the tubular body and each in fluid flow communication with the lumen through a one-way valve;

a one-way valve positioned within the lumen between the proximal end and inflatable cuff portions which permits distal fluid flow; and a valve on the distal end for permitting fluid flow outwardly of the tubular body.

* * * * *